(12) United States Patent
Liu et al.

(10) Patent No.: US 11,850,820 B2
(45) Date of Patent: *Dec. 26, 2023

(54) APERTURED NONWOVEN

(71) Applicant: The Procter & Gamble Company, Cincinnati, OH (US)

(72) Inventors: Xiaoxin Liu, Beijing (CN); Li Tang, Beijing (CN); Kun Sun, Beijing (CN); Fancheng Wang, Beijing (CN); Meng Chen, Beijing (CN)

(73) Assignee: The Procter and Gamble Company, Cincinnati, OH (US)

( * ) Notice: Subject to any disclaimer, the term of this patent is extended or adjusted under 35 U.S.C. 154(b) by 154 days.

This patent is subject to a terminal disclaimer.

(21) Appl. No.: 17/231,132

(22) Filed: Apr. 15, 2021

(65) Prior Publication Data

US 2021/0324554 A1 Oct. 21, 2021

(51) Int. Cl.
 *B32B 3/24* (2006.01)
 *A61F 13/511* (2006.01)
 (Continued)

(52) U.S. Cl.
 CPC ............ *B32B 3/266* (2013.01); *A61F 13/512* (2013.01); *A61F 13/5123* (2013.01); *A61F 13/5125* (2013.01); *A61F 13/5126* (2013.01); *B26F 1/24* (2013.01); *D04H 1/425* (2013.01); *D04H 1/492* (2013.01); *D04H 3/10* (2013.01); *D04H 13/001* (2013.01); *A61F 13/5146* (2013.01);
 (Continued)

(58) Field of Classification Search
None
See application file for complete search history.

(56) References Cited

U.S. PATENT DOCUMENTS 3,881,490 A 5/1975 Whitehead et al.
4,780,352 A * 10/1988 Palumbo ............... A61F 13/513
604/378

(Continued)

FOREIGN PATENT DOCUMENTS

CN 201106090 Y * 8/2008
CN 101818415 A * 9/2010
(Continued)

OTHER PUBLICATIONS

Machine Translation of CN-106811866-A, Jun. 2017 (Year: 2017).*
(Continued)

*Primary Examiner* — Jeffrey A Vonch
(74) *Attorney, Agent, or Firm* — Melissa G. Krasovec; George Henry Leal; Amanda Herman Berghauer

(57) ABSTRACT

An apertured nonwovens having a first nonwoven layer is described. The first nonwoven layer includes cellulose-based fibers and a plurality of apertures, wherein the plurality apertures have a minimum aperture distance between two adjacent apertures which has a relative standard deviation no greater than about 40%, as measured according to the Aperture Quality Test. The apertures have an aperture size no greater than about 2.2 mm$^2$ and have an occlusion no greater than about 9%, as measured according to the Aperture Quality Test, or the apertures have an aspect ratio no greater than about 2.5 as measured according to the Aspect Ratio Test.

19 Claims, 5 Drawing Sheets

(51) Int. Cl.
  *A61F 13/512* (2006.01)
  *A61F 13/514* (2006.01)
  *D04H 1/425* (2012.01)
  *D04H 1/492* (2012.01)
  *B32B 3/26* (2006.01)
  *D04H 13/00* (2006.01)
  *B26F 1/24* (2006.01)
  *D04H 3/10* (2012.01)

(52) U.S. Cl.
  CPC . *A61F 13/51121* (2013.01); *A61F 2013/5127* (2013.01); *A61F 2013/51143* (2013.01); *A61F 2013/51178* (2013.01); *A61F 2013/51452* (2013.01); *B32B 2262/062* (2013.01); *B32B 2262/065* (2013.01); *B32B 2262/08* (2013.01); *B32B 2555/02* (2013.01); *D10B 2401/022* (2013.01); *Y10T 428/24273* (2015.01); *Y10T 428/24322* (2015.01); *Y10T 428/24331* (2015.01); *Y10T 428/27* (2015.01)

(56) References Cited

U.S. PATENT DOCUMENTS

| | | | |
|---|---|---|---|
| 5,160,582 A | 11/1992 | Takahashi | |
| 5,660,882 A | 8/1997 | Mcbride et al. | |
| 5,753,342 A | 5/1998 | Mcbride et al. | |
| 5,919,178 A | 7/1999 | Widlund | |
| 5,990,376 A * | 11/1999 | Inoue | A61F 13/5148 604/378 |
| 6,224,811 B1 | 5/2001 | Powers et al. | |
| 6,452,064 B1 * | 9/2002 | Thoren | A61F 13/512 604/383 |
| 6,750,166 B1 * | 6/2004 | Etzold | D04H 1/54 28/103 |
| 7,005,558 B1 * | 2/2006 | Johansson | A61F 13/512 604/383 |
| 11,154,428 B2 | 10/2021 | Rosati et al. | |
| 2003/0050618 A1 * | 3/2003 | Kondo | A61F 13/537 604/385.03 |
| 2003/0114069 A1 * | 6/2003 | Scheubel | A47K 7/02 442/388 |
| 2004/0122396 A1 | 6/2004 | Maldonado et al. | |
| 2004/0209041 A1 * | 10/2004 | Muth | B32B 3/266 428/131 |
| 2005/0217091 A1 * | 10/2005 | Muth | D04H 1/544 28/106 |
| 2006/0121207 A1 | 6/2006 | Prodoehl et al. | |
| 2006/0141885 A1 * | 6/2006 | Cobbs | B32B 5/26 442/166 |
| 2009/0259208 A1 * | 10/2009 | Hellstrom | D04H 18/04 604/383 |
| 2009/0311481 A1 | 12/2009 | Morin et al. | |
| 2012/0080155 A1 | 4/2012 | Konishi et al. | |
| 2014/0296815 A1 * | 10/2014 | Takken | A61F 13/51104 604/383 |
| 2014/0324009 A1 * | 10/2014 | Lee | A61F 13/513 428/137 |
| 2015/0044926 A1 * | 2/2015 | Rahbaran | D04H 1/425 442/337 |
| 2015/0099086 A1 * | 4/2015 | Kim | A61F 13/5148 428/68 |
| 2016/0129626 A1 | 5/2016 | Arora et al. | |
| 2016/0129662 A1 * | 5/2016 | Arora | A61F 13/512 428/138 |
| 2016/0136014 A1 * | 5/2016 | Arora | A61F 13/511 428/137 |
| 2017/0000663 A1 | 1/2017 | Xu et al. | |
| 2017/0196414 A1 | 7/2017 | Erlandsson et al. | |
| 2017/0258647 A1 * | 9/2017 | Orr | D04H 3/007 |
| 2018/0169995 A1 * | 6/2018 | Zajaczkowski | B32B 3/266 |
| 2018/0229216 A1 * | 8/2018 | Smith | B32B 5/266 |
| 2018/0344539 A1 * | 12/2018 | Kurihara | A61F 13/512 |
| 2019/0117472 A1 * | 4/2019 | Erdem | A61F 13/512 |
| 2019/0240084 A1 * | 8/2019 | Rosati | A61F 13/5123 |
| 2020/0397628 A1 * | 12/2020 | Gwag | B32B 21/10 |
| 2021/0015685 A1 * | 1/2021 | Erdem | A61F 13/5116 |
| 2021/0267819 A1 * | 9/2021 | Sa | A61F 13/51108 |
| 2021/0324557 A1 | 10/2021 | Liu et al. | |
| 2022/0133551 A1 * | 5/2022 | Wang | A61F 13/51401 604/383 |

FOREIGN PATENT DOCUMENTS

| | | | | |
|---|---|---|---|---|
| CN | 103156735 A | * | 6/2013 | |
| CN | 106048888 A | * | 10/2016 | D04H 1/4242 |
| CN | 205711402 U | * | 11/2016 | A61F 13/51121 |
| CN | 106420183 A | | 2/2017 | |
| CN | 206151698 U | * | 5/2017 | |
| CN | 106811866 A | * | 6/2017 | A61F 13/472 |
| CN | 106906569 A | * | 6/2017 | D04H 1/4374 |
| CN | 107460634 A | | 12/2017 | |
| CN | 107475893 A | | 12/2017 | |
| CN | 107641896 A | | 1/2018 | |
| CN | 107938165 A | * | 4/2018 | |
| CN | 108049023 A | * | 5/2018 | A61F 13/496 |
| CN | 108103664 A | * | 6/2018 | D04H 1/4258 |
| CN | 108823816 A | * | 11/2018 | D04H 13/00 |
| CN | 109112725 A | * | 1/2019 | D04H 1/492 |
| CN | 110344174 A | | 10/2019 | |
| CN | 110344174 A | * | 10/2019 | B26F 1/24 |
| CN | 210012971 U | * | 2/2020 | D04H 1/492 |
| EP | 489205 A1 | * | 6/1992 | A61F 13/512 |
| EP | 1873289 A1 | | 1/2008 | |
| GB | 2103933 A | * | 3/1983 | A61F 13/15731 |
| JP | 03019950 A | * | 1/1991 | |
| JP | H04371149 A | | 12/1992 | |
| JP | 08024289 A | * | 1/1996 | |
| JP | 11028222 A | * | 2/1999 | A61F 13/51121 |
| JP | 2003000639 A | * | 1/2003 | |
| JP | 2005097782 A | * | 4/2005 | |
| JP | 2007070765 A | * | 3/2007 | D04H 18/02 |
| JP | 2009153740 A | | 7/2009 | |
| JP | 2009287158 A | * | 12/2009 | |
| JP | 2010059592 A | * | 3/2010 | |
| JP | 2010269029 A | * | 12/2010 | A61F 13/472 |
| WO | WO-2008120959 A1 * | 10/2008 | B26F 1/10 |
| WO | 2017164195 A1 | | 9/2017 | |
| WO | WO-2018055703 A1 * | 3/2018 | B26D 7/10 |
| WO | 2021007762 A1 | | 1/2021 | |

OTHER PUBLICATIONS

Machine Translation of CN-110344174-A, Oct. 2019 (Year: 2019).*
Machine Translation of JP-11028222-A, Feb. 1999 (Year: 1999).*
Machine Translation of CN-201106090-Y, Aug. 2008 (Year: 2008).*
Machine Translation of CN-205711402-U, Nov. 2016 (Year: 2016).*
Machine Translation of CN-108049023-A, May 2018 (Year: 2018).*
PCT Search Report and Written Opinion for PCT/CN2020/085097 dated Jan. 15, 2021, 10 pages.
PCT Supplementary International Search Report for PCT/CN2020/085097 dated Jul. 29, 2022, 11 pages.
All Office Actions, U.S. Appl. No. 17/231,047, filed on Apr. 15, 2021.

* cited by examiner

APERTURED NONWOVEN

FIELD OF THE INVENTION

The present invention relates to a nonwoven having apertures with high aperture quality, and absorbent article comprising the same.

BACKGROUND OF THE INVENTION

Nonwovens are widely used in a variety of absorbent articles for personal hygiene, such as disposable diapers for infants, training pants for toddlers, adult incontinence undergarments and/or sanitary napkins which are designed to absorb and contain body exudates, in particular large quantities of urine, runny bowel movement (BM) and/or menses.

Various nonwovens have been suggested for use as a component such as topsheets for absorbent articles from the standpoints of skin sensation, a feeling of dryness, comfort, absorption of expelled bodily fluids, and prevention of fluid flow-back.

It may be desirable that nonwovens have apertures as considered that nonwoven having apertures may have a breathable appearance, and delight users with a unique pattern especially when the apertures form a pattern.

Frequently, nonwovens used as a component of absorbent articles have apertures to improve performance of the article as well as to provide aesthetic visual impression. It may be desirable that nonwovens have apertures having a clean and clear shape and a regularity in size and/or shape to provide a desirable visual quality and efficient handling of body exudates. For some usages, it may be also desirable nonwovens comprise natural fibers. Apertured nonwoven containing cellulose-based fibers has been produced using spunlace aperturing process or water jet aperturing process. Spunlace aperturing process may form the mesh type apertured nonwoven design with relatively uniform apertures as the high pressure water jet can pass through material web uniformly distributed across all directions. However, spunlace aperturing process may not form a high clarity discrete aperture pattern as the pressure applied on web may not be uniform. It gets more challenging to form a high clarity discrete aperture pattern when the material basis weight is lower than 40 gsm and/or an aperture size is small.

As such, it is desirable to provide apertured nonwovens having clean and clear apertures.

As such, it is desirable to provide apertured nonwovens having apertures closely arranged so as to deliver a clearly perceived aperture pattern.

It is also desirable to provide apertured nonwoven having apertures fully developed as designed.

SUMMARY OF THE INVENTION

The present invention relates to a nonwoven comprising a first nonwoven layer which comprises cellulose-based fibers and a plurality of apertures, wherein the apertures have a minimum aperture distance between two adjacent apertures which has a relative standard deviation no greater than about 40%, as measured according to the Aperture Quality Test, and wherein the apertures have an aperture size no greater than about 2.2 mm² and an occlusion no greater than about 9%, as measured according to the Aperture Quality Test. The aperture size having an RSD no greater than about 60%.

The present invention also relates to a nonwoven comprising a first nonwoven layer which comprises cellulose-based fibers and a plurality of apertures, wherein the apertures have a minimum aperture distance between two adjacent apertures which has a relative standard deviation no greater than about 40%, as measured according to the Aperture Quality Test, and wherein the apertures have an aperture size no greater than about 2.2 mm² as measured according to the Aperture Quality Test, and wherein the apertures have an aspect ratio no greater than about 2.5, as measured according to the Aperture Quality Test.

The present invention also relates to a nonwoven comprising a first nonwoven layer comprising cellulose-based fibers and a plurality of apertures, the apertures formed by pin-hole aperturing, wherein the apertures have an RSD of minimum aperture distance between two adjacent apertures is no greater than about 40%, as measured according to the Aperture Quality Test.

The present invention also relates to an absorbent article comprising the nonwoven disclosed herein.

For ease of discussion, the apertured nonwoven and the absorbent article will be discussed with reference to the numerals referred to in these figures. The figures and detailed description should however not be considered limiting the scope of the claims, unless explicitly indicated otherwise, and the invention disclosed herein is also used in a wide variety of absorbent article forms.

BRIEF DESCRIPTION OF THE DRAWINGS

In the drawings, like numerals or other designations designate like features throughout the views.

DETAILED DESCRIPTION OF THE INVENTION

Figure 1A:
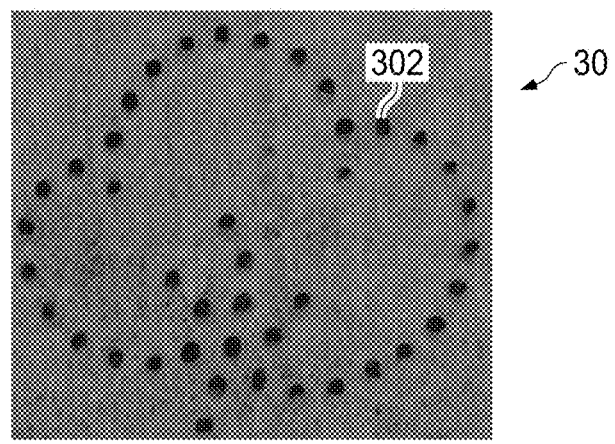
FIG. 1A is a microscopic image of an apertured nonwoven (Nonwoven 10) according to the present invention.

Various non-limiting forms of the present disclosure will now be described to provide an overall understanding of the principles of the structure, function, manufacture, and use of an absorbent article comprising back ears having unique engineering strain properties and low surface roughness. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments, feminine hygiene products such as sanitary napkins and pantyliners, and wipes.

The term "cellulose-based fibers", as used herein, intends to include both cellulose fibers such as pulp and cotton, and regenerated cellulose fiber such as rayon unless specified differently.

The term "forming elements", as used herein, refers to any elements on the surface of a forming member such as a roll, plate and belt that are capable of deforming a nonwoven.

As used herein, the term "natural fibers" refers to elongated substances produced by plants and animals and comprises animal-based fibers and plant-based fibers. Natural fibers may comprise fibers harvested without any post-harvest treatment step as well as those having a post-treatment step, such as, for example, washing, scouring, and bleaching.

As used herein, the term "plant-based fibers" comprises both harvested fibers and synthetic fibers that comprise bio-based content. Harvested plant-based fibers may comprise cellulosic matter, such as wood pulp; seed hairs, such as cotton; stem (or bast) fibers, such as flax and hemp; leaf fibers, such as sisal; and husk fibers, such as coconut.

Nonwoven

Nonwoven is useful in many fields, such as the hygiene field, the dusting and cleaning implement field, and the medical field, for example. In the hygiene field, nonwoven webs are used in absorbent articles, such as use as components in diapers, pants, adult incontinence products, tampons, liners, sanitary napkins, absorbent pads, bed pads, wipes, and various other products. Nonwoven may be used in absorbent articles as topsheets, outer cover nonwoven materials, portions of leg cuffs, acquisition materials, core wrap materials, portions of ears and side panels, portions of fastener tabs, portions of belts, and/or secondary topsheets, for example. The apertured nonwoven of the present disclosure may have particular application as a topsheet and/or an outer cover nonwoven material.

Nonwoven discussed herein comprises cellulose-based fibers. Nonwoven discussed herein optionally comprise natural fibers. Nonwoven discussed herein optionally comprises synthetic fibers. Fibers comprising the nonwoven of the present disclosure may be continuous and/or carded. Continuous fibers are generally longer fibers that are laid down in a random fashion in the nonwoven web, whereas carded fibers are generally shorter and have a decided directional lay within the nonwoven web.

Synthetic fibers for nonwovens discussed herein may comprise multi-constituent fibers, such as bi-component fibers or tri-component fibers, mono-component fibers, and/or other fiber types, for example. Multi-constituent fibers, as used herein, means fibers comprising more than one chemical species or material (i.e., multi-component fibers). Bi-component fibers are merely an example of multi-constituent fibers. The fibers may have round, triangular, tri-lobal, or otherwise shaped cross-sections, for example. In a continuous fiber or carded fiber context, it may be desirable to have fibers comprising more than one polymer component, such as bi-component fibers. Often, these two polymer components have different melting temperatures, viscosities, glass transition temperatures, and/or crystallization rates. As the multi-component fibers cool after formation, a first polymer component may solidify and/or shrink at a faster rate than a second polymer component, while the second polymer component may have sufficient rigidity to resist compression along a longitudinal fiber axis. The continuous fibers may then deform and curl up when strain on the fiber is relieved, thereby causing what is known as "crimp" in the fibers. Crimp of the fibers may aid in the softness and loft of a nonwoven web or topsheet, which is consumer desirable.

Bi-component fibers may comprise, for example, a first polymer component having a first melting temperature and a second polymer component having a second melting temperature. A first polymer component may comprise polypropylene and a second polymer component may comprise polyethylene, for example. As another example, a first polymer component may comprise polyethylene and a second polymer component may comprise polyethylene terephthalate. As yet another example, a first polymer component may comprise polyethylene and a second polymer component may comprise polylactic acid. If tri-component fibers are used, at least one polymer component may have a different melting temperature (in the ranges specified above) than a melting temperature of at least one of the other two polymer components. The fibers for the nonwoven disclosed herein may comprise petroleum sourced resins, recycled resins, or bio-sourced resins, such as polylactic acid from Nature Works and polyethylene from Braskem. The fibers may be or may comprise continuous fibers, such as spun-bond fibers and melt-blown fibers. Staple fibers, either petroleum-sourced or bio-sourced, such as cotton, cellulous, and/or regenerated cellulous may also be included in a nonwoven web. The multi-constituent fibers, such as bi-component fibers, may comprise sheath/core, side-by-side, islands in the sea, and/or eccentric configurations or may have other configurations.

Apertured Nonwoven

Figure 1B:
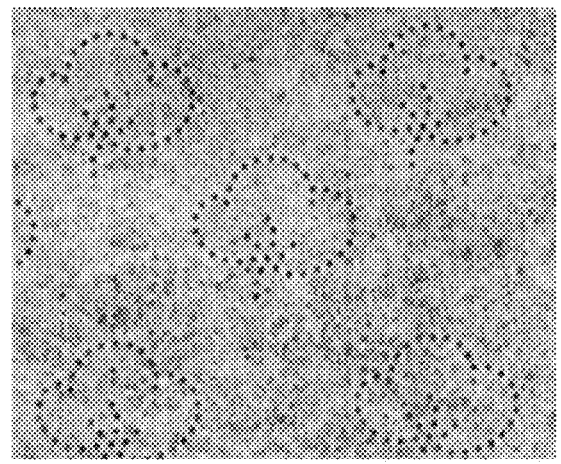
FIG. 1B is an image of an apertured nonwoven (Nonwoven 10) according to the present invention.

Nonwoven of the present invention comprises a first nonwoven layer comprising cellulose-based fibers and a plurality of apertures. FIG. 1A is a microscopic image of an apertured nonwoven 30 (Nonwoven 10) of the present invention comprising a plurality of apertures 302 and FIG. 1B is an image thereof.

In the first invention of the present invention, the first nonwoven layer comprises a plurality of apertures having a minimum aperture distance between two adjacent apertures which has an RSD no greater than 40%, as measured according to the Aperture Quality Test. The apertures have an aperture size no greater than about 2.2 mm$^2$, and an occlusion no greater than about 9%, as measured according to the Aperture Quality Test. The aperture size may have an RSD no greater than about 60%. The apertures may have an aperture aspect ratio no greater than about 2.5, as measured according to the Aperture Quality Test. The apertures may be formed by pin-hole aperturing.

In the second invention of the present invention, the first nonwoven layer comprises a plurality of apertures having a minimum aperture distance between two adjacent apertures which has an RSD no greater than about 40%, as measured according to the Aperture Quality Test. The apertures have an aperture size no greater than about 2.2 mm$^2$, and an aspect ratio no greater 2.5, as measured according to the Aperture Quality Test. The aspect ratio may have an RSD no greater than about 60%. The apertures may be formed by pin-hole aperturing.

In the third invention of the present invention, the first nonwoven layer comprises a plurality of apertures formed by pin-hole aperturing, the apertures having a minimum aperture distance between two adjacent apertures which has an RSD no greater than 40%, as measured according to the Aperture Quality Test. The apertures may have an aperture size no greater than about 2.2 mm$^2$, as measured according to the Aperture Quality Test. The aperture size may have an RSD no greater than about 60%. The apertures may have an aperture aspect ratio no greater than 2.5, as measured according to the Aperture Quality Test.

Nonwoven of the present invention may comprise apertures having an aperture size in the range of 0.1 mm$^2$-about 2.2 mm$^2$, or in the range of about 0.3 mm$^2$-about 2 mm$^2$, or in the range of about 0.5 mm$^2$-about 2.0 mm$^2$, or in the range of about 0.5 mm$^2$-about 1.5 mm$^2$ as measured according to the Aperture Quality Test. When an aperture size is too big, consumer may have negative perception on softness and leakage and she can see the absorbency layers under top sheet.

Nonwovens of the present invention may exhibit a highly regular geometric quality such that there is little variance in the size of apertures. For example, apertures in the nonwoven of the present invention may have an RSD of aperture size no greater than about 60%, no greater than about 50%, no greater than about 45%, or no greater than about 40%. This highly regular size of apertures represented by an RSD of aperture size may be important both for visual quality of the nonwoven web.

Apertured nonwovens according to the present invention may have apertures have a low aspect ratio no greater than about 2.5, or no greater than about 2, or no greater than about 1.8, or no greater than about 1.5, as measured according to the Aspect Ratio Test herein.

Nonwoven of the present invention may exhibit a highly regular geometric quality such that there is little variance in the shape of apertures. For example, apertures in the nonwoven of the present invention may have an aperture aspect ratio no greater than about 40%, no greater than about 30%, no greater than about 25%, or no greater than about 20%, as measured according to the Aspect Quality Test. This high degree of shape regularity represented by a low RSD of aspect ratio may be important both for visual quality of the nonwoven web.

Further, nonwoven according to the present invention may exhibit a higher aperture pattern clarity when indicated as a minimum aperture distance between two adjacent apertures and/or an RSD thereof. The apertures in the nonwoven of the present invention may have a minimum space between two adjacent apertures no greater than about 5 mm, or no greater than about 4.5 mm, no greater than about 4 mm, no greater than about 3.5 mm. When an Nonwoven of the present invention comprises a pattern comprising a plurality of apertures, this high degree of aperture pattern clarity represented by a small minimum aperture distance and/or a low relative standard deviation of minimum aperture distance may be important for visual quality as an apertured pattern may not be perceived as a complete graphic pattern when an minimum aperture distance and/or RSD of minimum aperture distance between adjacent apertures are too big.

Further, nonwoven according to the present invention may exhibit a higher aperture clarity when indicated as a percent occlusion. The nonwoven of the present invention comprises a plurality apertures which may have an occlusion no greater than about 9%, or no greater than about 8%, or no greater than about 7%, or no greater than about 6%, as measured according to the Aperture Clarity Test under Aperture Quality Test described herein. An aperture occlusion tends to increase when an aperture size get small, but the nonwoven of the present invention has apertures with a low occlusion despite a small aperture size of 2.2 mm$^2$ or less. Without wishing to be bound by theory, it is believed that improved aperture clarity may result in an apertured nonwoven with improved bodily exudate handling performance as well as an improved visible perception.

Nonwovens of the present invention comprises a first nonwoven layer comprising cellulose-based fibers and a plurality of apertures. The first nonwoven layer may comprise a discrete pattern formed by the plurality of apertures. With the term a discrete pattern herein, a nonwoven comprising a discrete pattern formed by apertures intends to exclude a mesh-type apertured nonwoven. In one embodiment, the discrete pattern may be a repeat pattern so that the nonwoven of the present invention comprises a plurality of repeat aperture patterns. The repeat pattern may repeat in random direction. The repeat pattern may repeat in a first direction. The repeat unit may repeat in a first direction and in a second direction which is different from the first direction. Repeat patterns may be in a same size or scale or may be a different size or scale. The repeat patterns may be in a same orientation. In some examples, the repeat patterns may be in a different orientation. In another embodiment, the pattern may be a continuous repeat pattern. The repeat pattern may be continuous in a first direction. The repeat unit may be continuous in a first direction and in a second direction which is different from the first direction. Repeat patterns may be in a same size or scale or may be in a different size or scale. The repeat patterns may be in a same orientation.

Nonwoven of the present invention may comprise a plurality of three dimensional elements such as protrusion and recesses, so that the apertured nonwoven has a three-dimensional structure.

The apertured nonwoven may define a second plurality of apertures, such that a first plurality of apertures and the second plurality of apertures form zones in the nonwoven. Each zone may comprise a plurality of apertures that may exhibit a highly regular geometric quality such that there is little variance in the aspect ratio as compared to another aperture within the same zone, but the aperture size varies between zones.

In the nonwoven of the present invention, the first nonwoven layer may comprises a spunlace web. The first nonwoven layer may comprise cellulose-based fibers selected from the group consisting of cotton fibers, regenerated cellulose-based fibers, and combinations thereof.

In the nonwoven of the present invention, the first nonwoven layer may comprise more than 50%, more than 60%, more than 70%, more than 80%, or more than 90% cellulose-based fibers by weight of the first nonwoven layer. In one embodiment, fibers in the first nonwoven layer comprise 100% cotton fibers.

The nonwoven of the present invention may further comprise a second nonwoven layer joined to the first nonwoven layer. The second nonwoven layer may comprise synthetic fibers.

Figure 2:
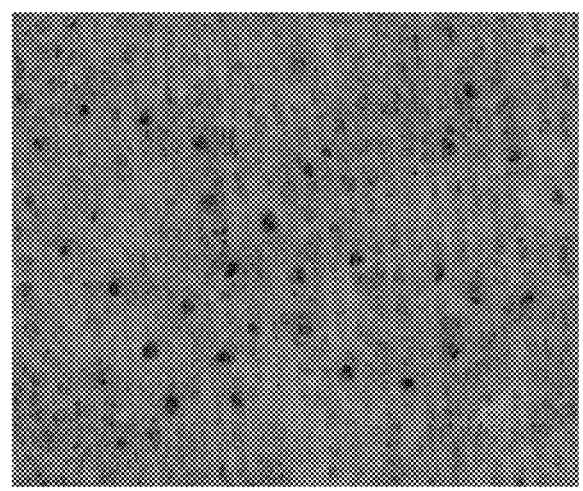
FIG. 2 is a microscopic image of an apertured nonwoven (Nonwoven 1).
Figure 3:
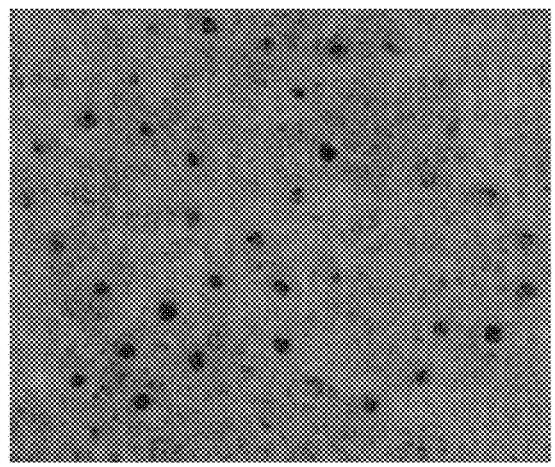
FIG. 3 is a microscopic image of an apertured nonwoven (Nonwoven 2).
Figure 4:
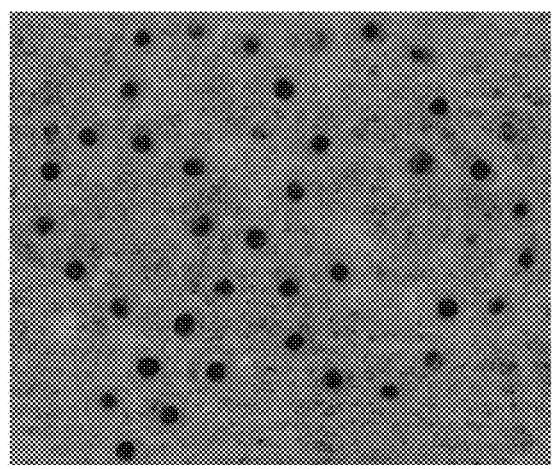
FIG. 4 is a microscopic image of an apertured nonwoven (Nonwoven 4) according to the present invention.
Figure 5:
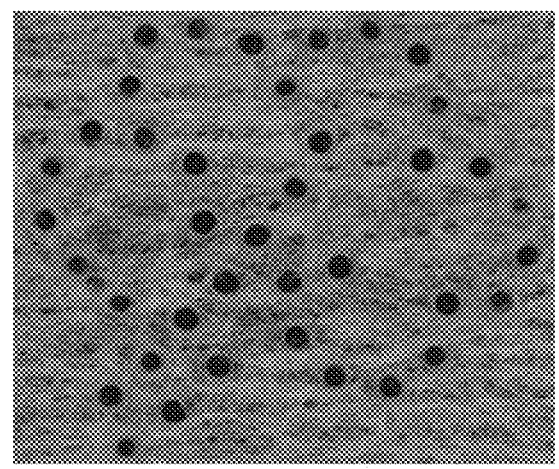
FIG. 5 is a microscopic image of an apertured nonwoven (Nonwoven 6) according to the present invention.
Figure 6A:
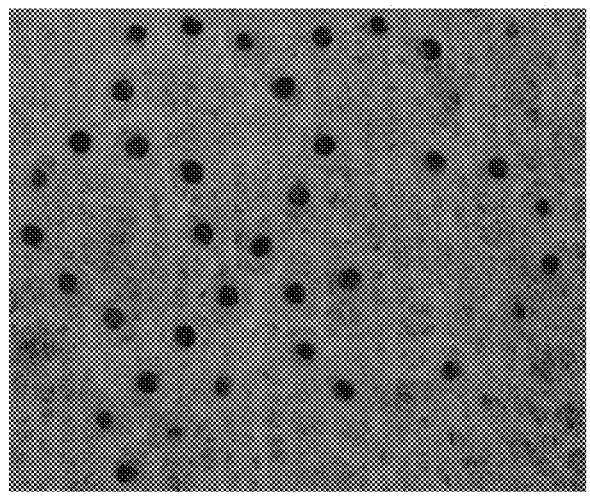
FIG. 6A is a microscopic image of an apertured nonwoven (Nonwoven 7) according to the present invention.
Figure 6B:
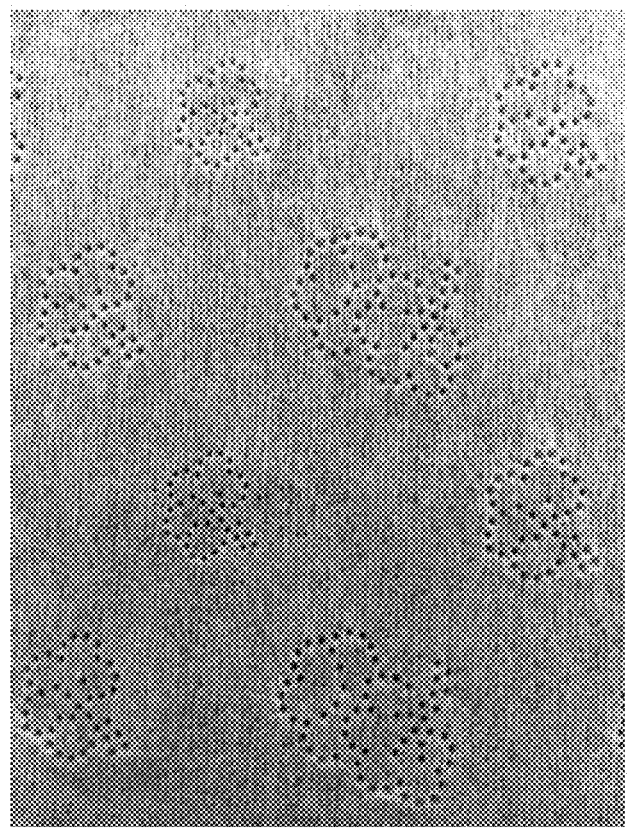
FIG. 6B is an image of an apertured nonwoven (Nonwoven 7) according to the present invention.
Figure 8:
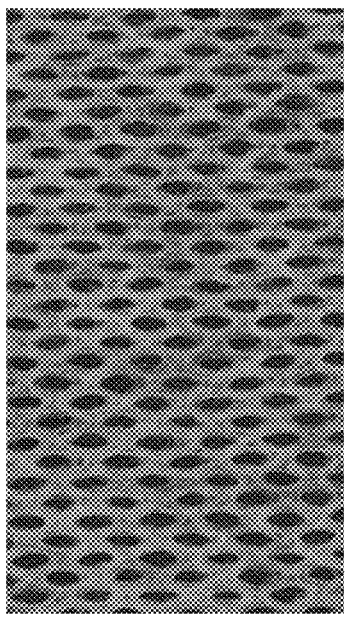
FIG. 8 is a microscopic image of a related art apertured nonwoven (Nonwoven 12).
Figure 9:
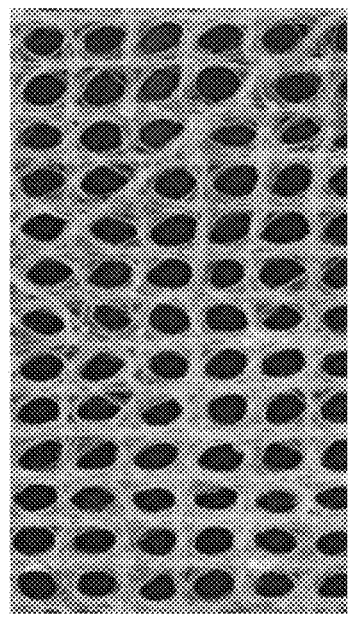
FIG. 9 is a microscopic image of a related art apertured nonwoven (Nonwoven 13).
Figure 7A:
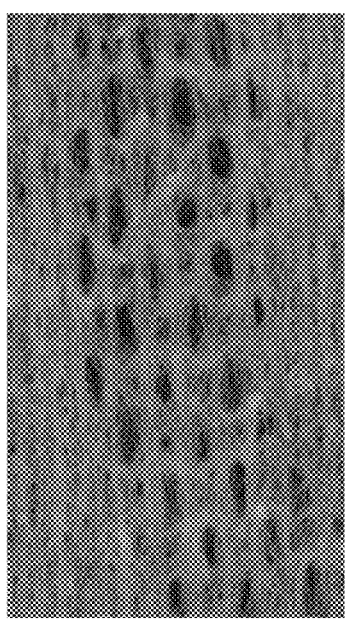
FIG. 7A is a microscopic image of a related art apertured nonwoven (Nonwoven 11).

FIG. 1 is a microscopic image of an apertured nonwoven (Nonwoven 10) of the present invention. Referring to FIG. 1, the apertured nonwoven 30 may define a plurality of apertures 302. FIGS. 2 and 3 are microscopic images of comparative apertured nonwovens, Nonwovens 1 and 2, respectively. FIGS. 4-6 are microscopic images of apertured nonwoven, Nonwovens 4, 6 and 7, respectively according to the present invention. FIGS. 7A, 8 and 9 are microscopic images of related art nonwovens, Nonwovens 11-13, respectively.

The nonwoven according to the present invention can be incorporated into, for example, an absorbent article. For example, an absorbent article may have a component such as a topsheet and/or an outer most sheet comprising the apertured nonwoven.

The apertured nonwoven may comprise a plurality of apertures over the entirety of the nonwoven, or may comprise a plurality of apertures over one or more discrete areas or zones of the nonwoven. The nonwoven may comprise two or more zones which each define a plurality of apertures, and the apertures exhibiting a high degree of regularity in shape and size within each zone, but having different sizes and/or different shapes between the zones. The apertures or embosses may also form any fanciful pattern in the nonwoven, An absorbent article of the present invention comprises the apertured nonwoven of the present invention. In one embodiment, the absorbent article comprises a topsheet comprising the apertured nonwoven of the present invention. Where the topsheet has more than one layer, only the first layer on the first side configured to face a wearer may comprise the apertured nonwoven of the present invention. A second layer may be unapertured layer, being hydrophilic. Alternatively, all layers of a multi-layered topsheet may be apertured. For example, a topsheet may comprise two apertured, hydrophobic nonwoven webs. In such case, the topsheet may be disposed in a face to face relationship with a hydrophilic acquisition layer. The topsheet may define a plurality of apertures over the entirety of the topsheet or may define a plurality of apertures over one or more discrete areas or zones of the topsheet. As an example, apertures may be formed only on the portion of the topsheet that overlaps the acquisition material or the absorbent core. The topsheet may comprise two or more zones which each define a plurality of apertures, the apertures exhibiting a high degree of regularity in shape and size within each zone, but having different sizes and/or different shapes Process for Producing Apertured nonwoven FIG. 9 is a schematic illustration of one example process for forming apertured nonwoven of the present disclosure. Referring to FIG. 9 depicting a simplified, schematic view of an exemplary process according to the present invention, nonwoven 20 is supplied to a water content adjustment unit 200 where a water content of nonwoven 20 is adjusted, so that the nonwoven 20 comprises at least one area having a water content of at least about 12%, or at least 20%, or at least about 30%, or at least about 40% by weight of the nonwoven in the area.

A water content of nonwoven 20 in the water content adjustment unit 200 may can be adjusted by for example, applying moisture to nonwoven 20 or drying nonwoven 20 using any known and suitable method.

In some embodiments, a water content of a nonwoven may be adjusted by applying moisture to the nonwoven. As one example, a water content of a nonwoven may be adjusted by moisturizing a nonwoven utilizing a chamber equipped with a moisture generation machine to make the chamber is filled with moistures. Nonwoven is supplied to and goes through the chamber, and the nonwoven gets moisturized while it passes the chamber so that the nonwoven has a water content in a target range. As another example, a water content of a nonwoven can be adjusted by moisturizing a nonwoven utilizing a water pipe with a plurality of nozzles. The water pipe may be positioned above a nonwoven to be moisturized, and water spray is applied through the nozzles to apply water so that the nonwoven has a water content in a target range. In some of such embodiments, the entire area of the nonwoven is moisturized.

In some embodiments, a water content of a nonwoven may be adjusted by drying the nonwoven to remove excess water from the nonwoven, for example when the process of the present invention is on-line process conducted continuously following hydroentanglement to produce a nonwoven web. Nonwoven from the hydroentanglement containing excess amount of water may be passed through a dewatering device such as a drying system where excess water is removed so that the nonwoven has a water content in a target range.

In some embodiments, a water content of at least one pre-determined region in a nonwoven may be adjusted by a positioned moisturizing process. For example, printing technology like flex printing or engraving printing well known in the industry can be used to print/supply water into specific determined region(s) on nonwoven so that the pre-determined regions are moisturized as desired.

Referring to FIG. 9, nonwoven 20 leaving the water content adjustment unit 200 may comprise at least one area having a water content of about at least 12%, or at least 20%, or at least about 30%, or at least about 40% by weight of the nonwoven in the area. In some embodiments, the entire area of nonwoven 20 is moisturized to have a water content of about at least 12%, or at least 20%, or at least about 30%, or at least about 40% by weight of the nonwoven. In other embodiments, nonwoven 20 comprises a plurality of moisturized areas, each moisturized area having a water content about at least 12%, or at least 20%, or at least about 30%, or at least about 40% by weight of the nonwoven in the area. The moisturized areas may be pre-determined areas where deformations are formed.

Fibers forming the nonwoven 20 can be of natural or man-made origin and may be staple fibers or continuous filaments or be formed in situ. The nonwoven 20 may comprise natural fibers at least 15%, or at least 20%, or at least 50%, or 100% by weight of the nonwoven. The natural fibers may be cellulose-based fibers. In some embodiments, fibers forming the nonwoven 20 are cellulose-based fibers.

The nonwoven 20 may comprise a single layer. It may comprise two or more layers, which may form a unitary structure or may remain as discrete layers which may be attached at least partially to each other by, for example, thermal bonding, adhesive bonding or a combination thereof. A unitary structure herein intends to mean that although it may be formed by several sub-layers that have distinct properties and/or compositions from one another, they are somehow intermixed at the boundary region so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition. Typically, there is no adhesive used between the sub-layers of the unitary material. However, in some cases, adhesives and/or binders can be present although typically in a lower amount that in multilayer materials formed by separate layers.

The nonwoven 20 may has a basis weight of 20 gsm-100 gsm, or 25 gsm-50 gsm, or 30 gsm-50 gms.

Referring to FIG. 9, nonwoven 20 leaving the water content adjustment unit 200 is transferred to a deformation unit 300 where the nonwoven 20 is mechanically deformed and dewatered to produce a apertured nonwoven 30.

Mechanical deformation of nonwoven may be conducted via various processes known to those skilled in the art. Mechanical deformation process may comprise a process using a deformation apparatus selected from the group consisting of an aperture forming process, a protrusion forming process, an embossing forming process and any combination thereof. Mechanical deformation of a nonwoven may be conducted using a mechanical deformation apparatus. Mechanical deformation apparatuses forming embossing and/or apertures are well known in the art such as WO2011/090974 and WO2015/134359. In some embodiments, a deformation process may comprise subjecting a nonwoven to a deformation apparatus, the deformation apparatus comprising a first forming member and a second forming member, and moving the nonwoven through a nip that is formed between the first and second forming members so that deformations are formed in the nonwoven as the first forming member and the second forming member are engaged. Although the apparatuses will be described herein for convenience primarily in terms of rolls, it should be understood that the description will be applicable to forming structures comprising a forming member that have any other suitable configurations.

Figure 10:
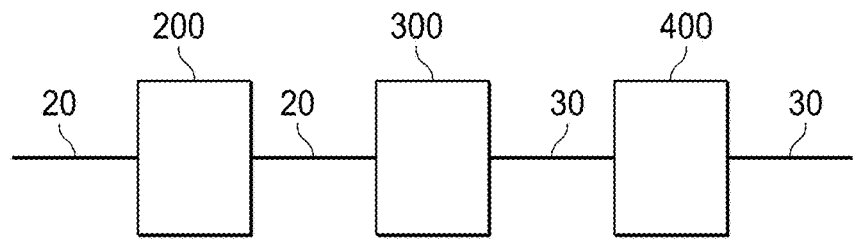
FIG. 10 is a schematic representation of an aperturing process for producing an apertured nonwoven.

FIG. 10 is a schematic illustration of an example of mechanical deformation of nonwoven. A nonwoven 20 is passed through a nip 502 formed by a pair of rolls 500, two intermeshing rolls 504 and 506, to form deformations in nonwoven web 20. The first roll 504 may comprise a plurality of first elements such as protrusions extending outwardly from the first roll 504. The first elements on the first roll 504 may be various in a size, shape, height, area, width and/or dimension which may determine the size, shape and dimension of deformations such as apertures and embossing. The second roll 506 may have a flat surface. Or, the second roll 506 may comprise grooves intermeshing with the protrusions of the first roll 504. When the nonwoven 20 comprises thermoplastic fibers, at least one of the rolls 504 and 506 may be heated to a temperature to soften fibers constituting the nonwoven 20 but lower than the melting point the fibers. When the fiber comprises a sheath/core type bicopolymer, at least one of the rolls 504 and 506 may be heated to a temperature higher than the melting point of the sheath polymer. In some embodiments, a first roll 504 may create the apertures (in combination with the second roll) and a second roll 506 may create projections (in combination with the first roll) in the nonwoven 20. The first roll 506 may comprise a plurality of first forming elements such as teeth, and a plurality of second recesses formed in a radial outer surface of the first roll 504. The second roll 506 may comprise a plurality of second forming element extending radially outwardly from the second roll 506 configured to at least partially engage with the second recesses in the first roll 504.

The nonwoven 20 mechanically deformed is dewatered to produce an apertured nonwoven. The nonwoven 20 may be dewatered by providing compression to the nonwoven. The nonwoven 20 may be dewatered by introducing heat to the nonwoven. Any of various heat sources known in the nonwoven manufacturing process such as a heated roller, oven, burner, and/or infrared radiation, and any combinations thereof can be employed to introduce heat to the nonwoven. For example, heat may be introduced to the nonwoven by directly contacting a hear source such as a heated roller to the nonwoven. Or, heat may be introduced to the nonwoven by providing a hot air using an oven or a burner to the nonwoven. The dewatered nonwoven may have a water content less than about 20%, or less than about 15%, or less than about 12%, or less than about 10%.

In the mechanical deformation process, mechanical deformation of a nonwoven may be conducted prior to dewatering the nonwoven. Or, mechanical deformation and dewatering a nonwoven may be carried out simultaneously. In some embodiments, referring to FIG. 14, the deformation process suitable for the present invention comprises subjecting the nonwoven to a deformation apparatus, the deformation apparatus comprising a first forming member and a second member, wherein the first forming member comprises first forming elements on its surface, wherein at least one of the first forming member and the second forming member is heated, and moving the nonwoven through a nip that is formed between the first and second forming members so that deformations are formed in the nonwoven as the first forming member and the second forming member are engaged, wherein the nonwoven contacts the first and second forming members for sufficient time the deformations are formed and dewatering of the nonwoven occurs.

In some embodiments, the deformation process comprises a pin-aperturing process. Referring to FIG. 10, a first roll 504 may comprise a plurality of first forming elements such as teeth being tapered from a base and a tip, the teeth being joined to the first roll. The second roll 506 may comprise a plurality of first recesses which intermesh with the first forming elements on the first roll at the nip. At least one of the rolls 504 and 506 may be heated to introduce enough heat to the nonwoven during a contact time to form apertures as intended and the moisture in the nonwoven can be evaporated. A roll temperature may be determined considering a contact time of the nonwoven and the heated roll. Though a low temperature such as 50° C. may be employed with an extended contact time, it may not be efficient applying to a high speed deformation process. Given a trend of high nonwoven production process, the first and/or second forming member such as a roll may be heated to a temperature higher than 70° C., or higher than 80° C., or higher than 100° C., or higher than 110° C., or higher than 120° C.

Figure 11:
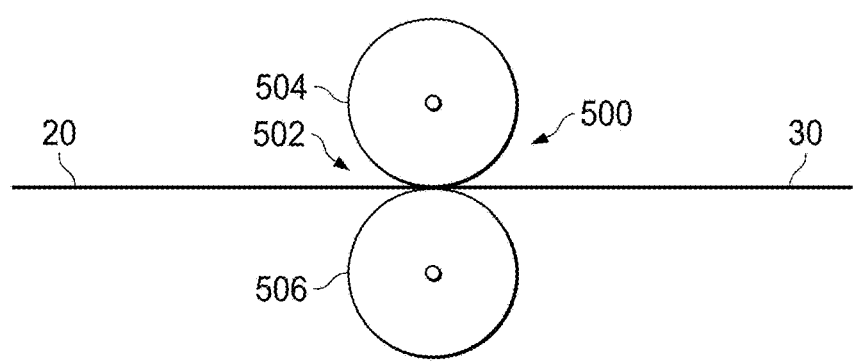
FIG. 11 is a schematic representation of a pin-hole aperturing.

Without wishing to be bound by theory, a water content of nonwoven may affect to deformation quality. In nonwoven comprising cellulose-based fibers, the cellulose-based fibers in a dry condition are connected via hydrogen bonds. When the nonwoven absorbs enough moisture, hydrogen bonds connecting fibers are released and the fibers get more flexible to move, so that nonwoven gets easier to be deformed. Prompt reduction of moisture in the mechanically apertured nonwoven while deformations formed in the nonwoven are maintained results in formation of new hydrogen bonds among fibers which may stabilize the deformation. Referring to FIG. 11, the apertured nonwoven 30 is optionally subjected to a drying unit 400 to further dry the apertured nonwoven 30. The apertured nonwoven 30 may be further dried to have a water or other solution content, less than about 10%, less than about 5%, or less than about 3% by weight to prevent an issue due to microorganism growth.

In some embodiments, an Nonwoven of the present invention may be produced by a process comprising (a) subjecting a fibrous web to an entanglement process to obtain a nonwoven, (b) adjusting a water content of the nonwoven in such a way that the nonwoven comprises at least one area having a water content of at least 12% by weight of the nonwoven, and (c) subjecting the nonwoven to a mechanical deformation process to produce a apertured nonwoven. The entanglement process is a hydroentanglement process or a needle punching process. The (b) and the (c) steps may be carried out simultaneously.

FIG. 11 depicts a simplified, schematic view of another exemplary process to produce an nonwoven according to the present invention. Referring to FIG. 11, a fibrous web 10 is supplied to an entanglement unit 100 for fiber entanglement to produce a nonwoven web 20. The nonwoven 20 is supplied to a water content adjustment unit 200 where a water content of the nonwoven 20 is adjusted so that the nonwoven 20 comprises at least one area having a water content of a least about 12% by weight of the nonwoven in the area. The nonwoven 20 is subjected to a deformation unit 300 to mechanically deform the nonwoven and dewater the nonwoven. Still referring to FIG. 11, the apertured nonwoven 30 may be subjected to a drying unit 400 to dry the apertured nonwoven 30 to have a water content of less than 10% by weight of the nonwoven.

The fiber entanglement in the entanglement unit 100 can be carried out by any method known for fiber entanglement such as a needle punching method, a hydro-entangling method, a water vapor flow (steam jetting) entangling method, and the like. In some embodiments, the fiber entanglement is carried out using a hydroentangling method.

Descriptions with respect to the deformation process and drying process with respect to the process of FIG. 9 above apply to the process of FIG. 11.

Figure 12:
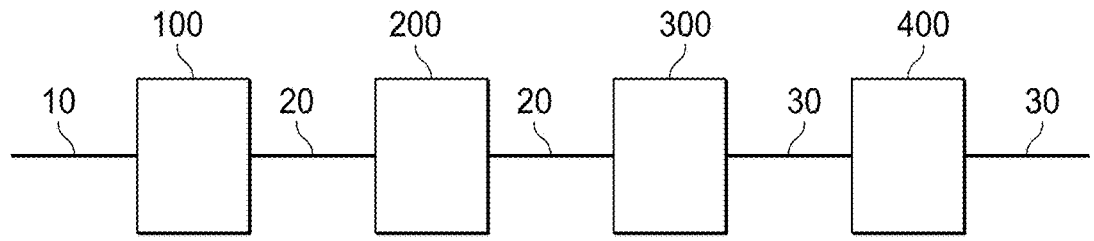
FIG. 12 is a schematic representation of another aperturing process for producing an apertured nonwoven.
Figure 13:
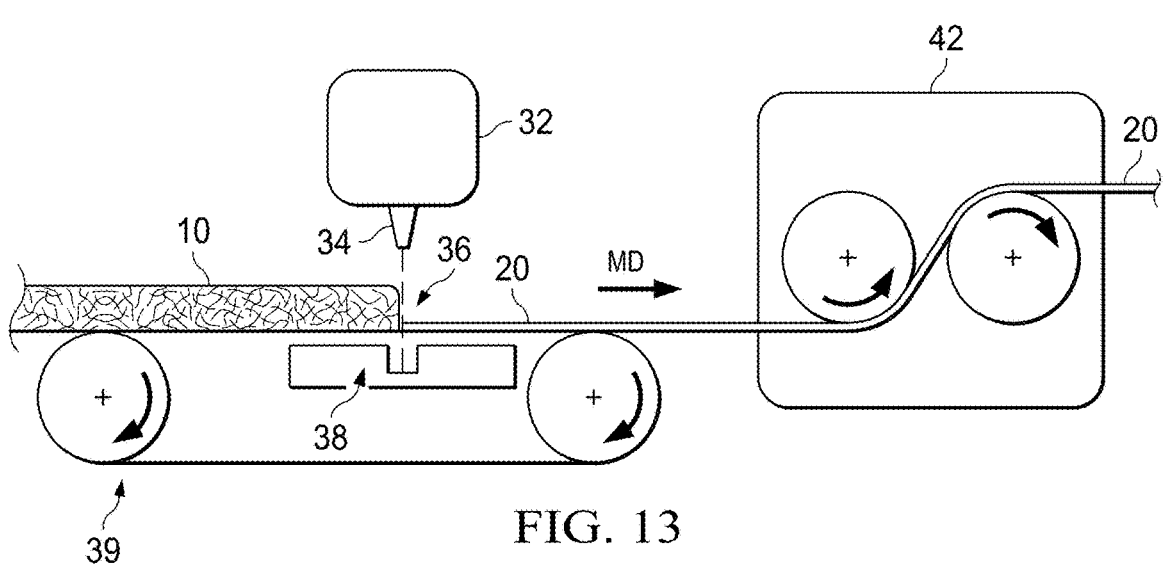
FIG. 13 is a schematic representation of a hydroentanglement process.

FIG. 12 depicts a simplified, schematic view of one example hydroentangled nonwoven manufacturing process. As is generally known in the art, hydroentanglement (sometimes referred to as spunlacing, jet entanglement, water entanglement, hydroentanglement or hydraulic needling), is a mechanical bonding process whereby fibers of a nonwoven web are entangled by means of high pressure water jets. Patterning can be achieved by use of patterned drums or belts which cause the fibers to form a negative image of the drum design in the fabric. The formed web of various fibrous components (usually airlaid, wetlaid, or carded, but sometimes spunbond or melt-blown, etc.) can first be compacted and prewetted to eliminate air pockets and then water-needled. With reference to FIG. 12, a fibrous web 10 upstream of a jet head 32 passes under the jet head 32 and go through hydroentanglement. During the entanglement process, the fibrous web 10 is passed by the jet head 32 that comprises a plurality of injectors that are positioned to generally form a water curtain (for simplicity of illustration, only one injector 34 is illustrated in FIG. 12). A water jet 36 is directed through the fibrous web 10 at high pressures, such as 150 or 400 bar. As is to be appreciated, while not illustrated, multiple rows of injectors 34 are typically used, which can be positioned on one or both sides of the fibrous web 10. Hydroentangled nonwoven 20 can be supported by any suitable support system 39, such as a moving wire screen (as illustrated) or on a rotating porous drum, for example. While not illustrated, it is to be appreciated that hydroentanglement systems can expose the fibrous web 10 to a series of jet heads 32 along the machine direction, with each delivering water jets at different pressures. The particular number of jet heads 32 utilized can be based on, for example, desired basis weight, degree of bonding required, characteristics of the web, and so forth. As the water jet 36 penetrates the web, a suction slot 38 positioned proximate beneath the fibrous web 10 collects the water so that it can be filtered and returned to the jet head 32 for subsequent injection. The water jet 36 delivered by the jet head 32 exhausts most of its kinetic energy primarily in rearranging fibers within the fibrous web 10 to turn and twist the fibers to form a series of interlocking knots.

Once the fibrous web 10 has been hydroentangled, the nonwoven 20 is then passed through a dewatering device 42 where excess water is removed. The dewatering device 42 can be any suitable dewatering system including a drying system such as a multi-segment multi-level bed dryer, a vacuum system, and/or an air drum dryer, for example. The dewatering device 42, serves to dewater and dry the nonwoven 20, so that the nonwoven 20 has a water content (in the range of from about 20 wt % to about 70 wt %. The apertured nonwoven 30 after being dried may be further treated with additional heat especially when the nonwoven includes synthetic fibers. The synthetic fibers begin to soften, and these softened fibers touch each other, bonds will form between the fibers, thereby increasing the overall flexural rigidity of the structure due to the formation of these bond sites.

Absorbent Article

The present invention also provides an absorbent article comprising a layer comprising a nonwoven or a laminate according to the present invention.

The absorbent article of the present invention may comprise a topsheet and a backsheet joined to the topsheet. The absorbent article of the present invention may further comprise an absorbent core disposed between the topsheet and the backsheet. In some embodiments, the absorbent article of the present invention comprises a topsheet or a layer disposed below the topsheet comprising a nonwoven or a laminate according to the present invention.

The absorbent articles of the present invention may be produced industrially by any suitable means. The different layers may thus be assembled using standard means such as embossing, thermal bonding, gluing or any combination thereof.

Topsheet

Topsheet can catch body fluids and/or allow the fluid penetration inside the absorbent article. With the nonwoven according to the present invention, the first web layer is preferably, disposed on a side in contact with the skin.

Backsheet

Any conventional liquid impervious backsheet materials commonly used for absorbent articles may be used as backsheet. In some embodiments, the backsheet may be impervious to malodorous gases generated by absorbed bodily discharges, so that the malodors do not escape. The backsheet may or may not be breathable.

Absorbent Core

It may be desirable that the absorbent article further comprises an absorbent core disposed between the topsheet and the backsheet. As used herein, the term "absorbent core" refers to a material or combination of materials suitable for absorbing, distributing, and storing fluids such as urine, blood, menses, and other body exudates. Any conventional materials for absorbent core suitable for absorbent articles may be used as absorbent core.

Measurement

1. Water Content Measurement

Water content is measured using ISO method ISO 287: 2017 specifying an oven-drying method for the determination of the water content of nonwoven.

2. Microscopic Image

Microscopic images of specimens are taken using an Optical Microscope such as VR-3200 (KEYENCE, Japan) or equivalent. An appropriate magnification and working distance are chosen such that the aperture is suitably enlarged for measurement. The image is analyzed using ImageJ software (version 1.52e or above, National Institutes of Health, USA) to measure an aperture size.

3. Aperture Quality Test (1) Sample Preparation

When a nonwoven is available in a raw material form, a specimen with a size of 50 mm×50 mm is cut from the raw material. When a nonwoven is a component of a finished product, the nonwoven is removed from the finished product using a razor blade to excise the nonwoven from other components of the finished product to provide a nonwoven specimen with a size of 50 mm×50 mm A cryogenic spray (such as Cyto-Freeze, Control Company, Houston TX) may be used to remove the nonwoven specimen from other components of the finished product, if necessary.

(2) Image Generation

Aperture quality such as aperture size, aperture aspect ratio, aperture rate, and aperture clarity measurements for a nonwoven are performed on images generated by placing the specimen flat against a dark background under uniform surface lighting conditions and acquiring a digital image using an optical microscope such as Keyence 3D Measurement System VR-3200 or equivalent. Analyses are performed using image analysis program such as ImageJ software (version 1.52p or above, National Institutes of Health, USA) and equivalent. The image needs to be distance calibrated with an image of the ruler to give an image resolution, i.e. 67.8 pixels per mm After performing an auto-focus step, the microscope acquires a specimen image with a rectangular field of view that includes an aperture region, which is a region containing i) one entire discrete apertured pattern, or ii) at least 35 mm×20 mm area containing at least 20 apertures, whichever is available.

(3) Image Analysis—Binary Image

Open a specimen image in ImageJ Convert the image type to 8 bit. The 8-bit grayscale image is then converted to a binary image (with "black" foreground pixels corresponding to the aperture regions) using the "Minimum" thresholding method: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of openings and the lighter pixel peak of the specimen material. If the histogram contains either zero or one local maximum, the method cannot proceed further, and no output parameters are defined.

(4) Aperture Size, Aspect Ratio, Aperture Rate and Opening Rate

Set the scale according to the image resolution. Create a filtered image by removing small openings in the binary image obtained in (3) Image Analysis above using an outlier removing median filter, which replaces a pixel with median of the surrounding area of 5 pixels in radius if the pixel is darker than the surrounding. Create a second filtered image based on the first one by removing stray fibers in the binary image using an outlier removing median filter, which replaces a pixel with the median of the surrounding area of 5 pixels in radius if the pixel is brighter than the surrounding. Set the measurements to include the analysis of aperture area and shape descriptor (i.e. aspect ratio, which is the ratio between the major and minor axis length of a fitted ellipse, after replacing an area selection with the best fit ellipse by keeping the same area, orientation and centroid as the original selection). Obtain the area and aspect ratio values of selected openings ("quality apertures") after tracing openings by their outer edge and excluding the openings with size below 0.10 mm$^2$ and incomplete openings at the edge of acquired image.

(4-1) Aperture Size

Area values for all the quality apertures are analyzed to calculate the mean and standard deviation of the aperture size to the nearest 0.01 mm$^2$. The mean aperture size is reported as aperture size. The relative standard deviation (RSD, defined as the standard deviation divided by the mean and multiplied by 100) of the area values for all the quality apertures is calculated to the nearest 1%.

(4-2) Aspect Ratio

Aspect ratio values for all the quality apertures are analyzed to calculate the mean and standard deviation of the aspect ratio to the nearest 0.01 as describing the aperture shape. The mean aspect ratio is reported as aspect ratio. The relative standard deviation (RSD, defined as the standard deviation divided by the mean and multiplied by 100) of the aspect ratio values for all the quality apertures is calculated to the nearest 1%.

(4-3) Aperture Rate

Aperture rate is obtained by the equation below.

Aperture rate=(number of quality apertures/number of target apertures)×100

The number of target apertures herein means the total number of apertures intended to form which may be determined by tooling designs such as number of pins in a pin-aperturing apparatus. The number of quality apertures is divided by the number of target apertures and multiplied by 100 to give the result of aperture rate. Prepare and analyze a total of five substantially similar replicate samples. The reported values will be the arithmetic mean of the five replicate samples to the nearest 1%.

(4-4) Opening Rate

Divide the sum of the area values of all the quality apertures by the area of the rectangular field of view for one specimen image, and multiplied by 100 to calculate the opening rate. Prepare and analyze a total of five replicate samples in the same view size. The reported values will be the arithmetic mean of the five replicate samples to the nearest 0.01%.

(4-5) Minimum Aperture Distance

For all the quality apertures, using the recorded location of each aperture's centroid (that is the center point of the aperture as given by the average of the x and y coordinates of all of the pixels in the aperture area selection), the Euclidian distance between each aperture's centroid to all the other aperture centroids is calculated. For each quality aperture, the shortest (minimum) distance is then identified and recorded as a nearest neighbor distance. Nearest neighbor distances above 1 mm are selected for analysis.

The arithmetic mean of the selected nearest neighbor distances within the field of view is calculated and reported as the Minimum Aperture Distance to the nearest 0.1 mm. The standard deviation (SD) and relative standard deviation (RSD, defined as the standard deviation divided by the mean and multiplied by 100) of the recorded nearest neighbor distance values within the field of view are calculated and reported as the SD or RSD of Minimum Aperture Distance to the nearest 0.1 mm or 1% respectively.

(5) Aperture Clarity

Aperture clarity is determined by the measurement of percent occlusion (i.e. the percentage of the aperture area occluded by stray fibers.) Create a filtered image by removing small openings in the binary image generated in (3) Image Analysis—Binary Image using an outlier removing median filter, which replaces a pixel with the median of the surrounding area of 6 pixels in radius if the pixel is darker than the surrounding. Remove the stray fibers from apertures using a morphological closing filter, which performs a dilation operation followed by an erosion operation under the settings of one adjacent foreground (or background) pixel for dilation (or erosion) and pad edges when eroding, before filling the remaining holes in the apertures. Subtract the original binary image from the filtered image, keeping only positive values to show the stray fibers within apertures and measure the total area of stray fibers. The total area of stray fibers is then divided by the total area of apertures from the filtered image and multiplied by 100 to give the result of percent occlusion reported as aperture clarity to the nearest 0.01%.

EXAMPLES

Example 1: Preparation of Apertured Nonwovens

Nonwoven 1: 35 gsm spunlace 100% cotton nonwoven (CHTC, China) without moisturizing was supplied. Water content of the nonwoven measured by Water content Measurement disclosed herein, was 8% by weight of the nonwoven. The nonwoven was continuously proceeded with a pin aperturing process using an apparatus to form a plurality of apertures to obtain nonwoven 1. A temperature of pins in the apparatus was 105° C., and contact time of the nonwoven at tooling was 20 seconds. FIG. 2 is a microscopic image of nonwoven 1 taken according to the Microscopic Image under MEASUREMENT.

Nonwoven 2: 35 gsm spunlace 100% cotton nonwoven was supplied and moisturized so that the nonwoven has a water content of 20%. The nonwoven was continuously proceeded with a pin aperturing process using the same aperturing apparatus and process as used to produce nonwoven 1. FIG. 3 is a microscopic image of Nonwoven 2 taken according to the Microscopic Image under MEASUREMENT.

Nonwovens 3-5: Nonwovens 3-5 were produced using the same nonwoven, aperturing apparatus and process as used to produce Nonwoven 2 except for using water contents of 32%, 40% and 53%, respectively. FIG. 3 is a microscopic image of Nonwoven 4 taken according to the Microscopic Image under MEASUREMENT.

Nonwoven 6: Nonwoven 6 was produced using the same aperturing apparatus and process as used to produce nonwoven 2 except using 35 gsm 100% rayon (from Beijing Dayuan) instead of 35 gsm 100% cotton and a water content of 55%. FIG. 5 is a microscopic image of Nonwoven 6 taken according to the Microscopic Image herein.

Nonwovens 7-9: Nonwovens 7-9 were produced using the same nonwoven, aperturing apparatus and process used to produce Nonwoven 2 under deformation conditions described in Table 1 below. FIG. 6A is a microscopic image of Nonwoven 7 taken according to the Microscopic Image under MEASUREMENT, and FIG. 6B is an image of the same nonwoven. FIG. 6B shows three apertured pattern with different sizes, and one of patterns in a middle size was selected for FIG. 6A.

Nonwoven 10: Nonwoven 10 was produced using 35 gsm spunlace 100% cotton nonwoven by moisturizing the nonwoven to have a water content of 16%, and conducting a pin-aperturing under deformation conditions described in Table 1. FIG. 1 is a microscopic image of Nonwoven 10 taken according to the Microscopic Image under MEASUREMENT.

Figure 7B:
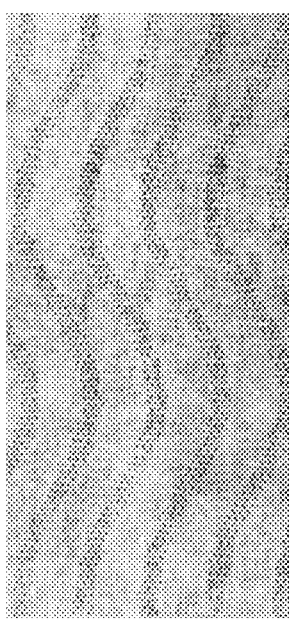
FIG. 7B is an image of a related art apertured nonwoven (Nonwoven 11) of a related art.

Nonwoven 11: 35 gsm 100% cotton nonwoven was produced using a water jet punching process to obtain Nonwoven 11. FIG. 7 is microscopic images of Nonwoven 11 taken according to the Microscopic Image under MEASUREMENT.

Nonwovens 12 and 13: Two commercially available 100% cotton nonwovens, Nonwoven 12 (Jacob Holm Industrials) and Nonwoven 13 (Winner Medical Co., Ltd.) were obtained. Both are 35 gsm, and have mesh-shape aperture patterns. FIGS. 8 and 9 are microscopic images of Nonwovens 12 and 13 respectively taken according to the Microscopic Image under MEASUREMENT.

Example 2: Nonwoven Characteristics

Number of quality apertures, aperture sizes, aperture aspect ratios, aperture rates, aperture, minimum aperture distance, and aperture clarity (occlusion) of nonwovens prepared in Example 1 were measured according to Aperture Quality Test under MEASUREMENT, and are indicated in Table 1 below.

Image field-of-view sizes are 31 mm×26 mm for Nonwovens 1-9; 37 mm×33 mm for Nonwoven 10; and 36 mm×20 mm for Nonwovens 11-13;

TABLE 1

| | Nonwoven | | | | | | |
| --- | --- | --- | --- | --- | --- | --- | --- |
| | 1 | 2 | 3 | 4 | 5 | 6 | 7 |
| Deformation process | Pin aperturing | | | | | | |
| NW Water content (%) | 8 | 20 | 32 | 40 | 53 | 55 | 44 |
| Pin temperature (° C.) | 105 | 105 | 105 | 105 | 105 | 105 | 48 |
| Contact time (s) | 20 | 20 | 20 | 20 | 20 | 20 | 300 |
| Image | FIG. 2 | FIG. 3 | | FIG. 4 | | FIG. 5 | FIG. 6A |
| No. of target aperture | 39 | 39 | 39 | 39 | 39 | 39 | 39 |
| No. of quality aperture | 9 | 10 | 26 | 37 | 34 | 40 | 38 |
| Aperture rate (%) | 23 | 26 | 67 | 95 | 87 | >100 | 97 |

TABLE 1-continued

| Aperture size (mm²) | 0.16 | 0.23 | 0.35 | 0.61 | 0.63 | 0.98 | 0.56 |
|---|---|---|---|---|---|---|---|
| SD of aperture size (mm²) | 0.05 | 0.12 | 0.16 | 0.21 | 0.30 | 0.32 | 0.24 |
| RSD of aperture size (%) | 31 | 52 | 46 | 34 | 48 | 33 | 43 |
| Aspect ratio | 1.57 | 1.42 | 1.31 | 1.21 | 1.27 | 1.20 | 1.37 |
| SD of aspect ratio | 0.26 | 0.10 | 0.19 | 0.19 | 0.29 | 0.21 | 0.51 |
| RSD of aspect ratio (%) | 17 | 7 | 15 | 16 | 23 | 18 | 37 |
| Minimum aperture distance (mm) | 5.6 | 5.4 | 3.5 | 3.1 | | | |
| SD of minimum aperture distance (mm) | 2.7 | 3.7 | 1.0 | 0.1 | | | |
| RSD of minimum aperture distance (%) | 48 | 69 | 29 | 3 | | | |
| Opening Rate (%) | 0.18 | 0.29 | 1.16 | 2.80 | 2.66 | 4.87 | 2.62 |
| Occlusion (%) | 6.50 | 5.93 | 5.36 | 4.41 | 5.02 | 4.15 | 5.74 |

| | Nonwoven | | | | | |
|---|---|---|---|---|---|---|
| | 8 | 9 | 10 | 11 | 12 | 13 |
| Deformation process | Pin aperturing | | | Water-jet aperturing | | |
| NW Water content (%) | 40 | 40 | 16 | NA | NA | NA |
| Pin temperature (° C.) | 78 | 88 | 150 | NA | NA | NA |
| Contact time (s) | 20 | 20 | 0.5 | NA | NA | NA |
| Image | | | FIG. 1A | FIG. 7A | FIG. 8 | FIG. 9 |
| No. of target aperture | 39 | 39 | 42 | | | |
| No. of quality aperture | 29 | 30 | 42 | 40 | 148 | 74 |
| Aperture rate (%) | 74 | 77 | 100 | | | |
| Aperture size (mm²) | 0.43 | 0.40 | 1.03 | 0.55 | 0.95 | 2.58 |
| SD of aperture size (mm²) | 0.25 | 0.21 | 0.24 | 0.52 | 0.23 | 0.98 |
| RSD of aperture size (%) | 58 | 53 | 23 | 95 | 24 | 38 |
| Aspect ratio | 1.49 | 1.34 | 1.25 | 3.32 | 2.75 | 1.79 |
| SD of aspect ratio | 0.59 | 0.18 | 0.17 | 1.50 | 0.52 | 0.52 |
| RSD of aspect ratio (%) | 40 | 13 | 14 | 45 | 19 | 29 |
| Minimum aperture distance (mm) | 3.3 | | | | | |
| SD of minimum aperture distance (mm) | 0.7 | | | | | |
| RSD of minimum aperture distance (%) | 21 | | | | | |
| Opening rate (%) | 1.56 | 1.49 | 3.53 | 3.04 | 19.52 | 26.49 |
| Occlusion (%) | 3.28 | 4.15 | 4.89 | 9.17 | 10.82 | 1.94 |

Nonwovens 1 and 2, comparison nonwovens, have apertures having minimum aperture distances between two adjacent apertures which have RSD greater than 40% as measured according to the Aperture Quality Test.

Nonwovens 3-10 of the present invention have apertures having have minimum aperture distances between two adjacent apertures which have RSD no greater than 40% as measured according to the Aperture Quality Test. The apertures have an aperture size no greater than about 2.2 mm² as measured according to the Aperture Quality Test, and an RSD of aperture size no greater than about 60%. The apertures have an aperture aspect ratio less than about 2.5, and an occlusion less than 9% as measured according to the Aperture Quality Test. With high aperture shape regularity and size regularity, nonwovens of the present invention provide clear aperture patterns.

Nonwoven 11, a related art nonwoven, has apertures having of an aperture size which has an RSD greater than 60%. The apertures have an aspect ratio greater than 2.5 and an occlusion higher than 9% as measured according to the Aperture Quality Test.

Nonwoven 12, a related art nonwoven, has apertures having an aperture aspect ratio greater than 2.5, and an occlusion higher than 9% as measured according to the Aperture Quality Test.

Nonwoven 13, a related art nonwoven, has apertures having an aperture size greater than 2.2 mm² as measured according to the Aperture Quality Test.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven comprising:
   a first nonwoven layer comprising cellulose-based fibers, wherein the first nonwoven layer comprises a plurality of apertures, the plurality of apertures formed by mechanically aperturing at least one moisturized area having a water content of at least about 20% by weight of the nonwoven in the moisturized area, prior to aperturing, and a plurality of apertures, wherein the plurality apertures have a minimum aperture distance between two adjacent apertures which has a relative standard deviation no greater than about 40%, wherein the apertures have an aperture size no greater than about 2.2 mm$^2$, the aperture size having a relative standard deviation no greater than about 60%, and wherein the apertures have an occlusion no greater than about 9%, wherein a mean of shortest distances, the shortest distance being between an aperture's centroid and the centroid of its nearest neighboring aperture and above 1 mm, is calculated as the minimum aperture distance and the standard deviation of the shortest distances divided by the mean and multiplied by 100 is the relative standard deviation;

wherein a mean of aperture areas is calculated as aperture size and the standard deviation of the aperture areas divided by the mean and multiplied by 100 is the relative standard deviation; and wherein a total area of stray fibers within apertures divided by a total area of apertures and multiplied by 100 is the percent occlusion, provided that apertures with sizes below 0.10 mm$^2$ and incomplete openings are excluded.

2. The nonwoven according to claim 1, wherein the standard deviation of aperture aspect ratios divided by the mean of aperture aspect ratios and multiplied by 100 is the relative standard deviation of the aperture aspect ratios, wherein the relative standard deviation is no greater than about 40%.

3. The nonwoven according to claim 1, wherein the apertures are formed by pin-hole aperturing.

4. The nonwoven according to claim 1, wherein the plurality of apertures form a discrete aperture pattern.

5. The nonwoven according to claim 4, wherein the discrete aperture pattern is a repeat discrete aperture pattern.

6. The nonwoven according to claim 1, wherein the apertures have an occlusion no greater than about 8%.

7. The nonwoven according to claim 1, wherein the apertures have an aperture size in the range of about 0.3 mm$^2$-about 1.5 mm$^2$.

8. The nonwoven according to claim 1, wherein the apertures have a minimum aperture distance no greater than about 5 mm.

9. The nonwoven according to claim 1, wherein the first nonwoven layer comprises a spunlace web.

10. The nonwoven according to claim 1, wherein the first nonwoven layer comprises more than 50% cellulose-based fibers by weight of the first nonwoven layer.

11. The nonwoven according to claim 1, wherein the cellulose-based fibers is selected from the group consisting of cotton fibers, regenerated cellulose-based fibers, and combinations thereof.

12. The nonwoven of claim 1, wherein the nonwoven further comprises a second nonwoven layer joined to the first nonwoven layer.

13. The nonwoven of claim 12, wherein the second nonwoven layer comprises synthetic fibers.

14. The nonwoven of claim 12, wherein the first nonwoven layer is hydrophilic.

15. An absorbent article comprising a liquid permeable topsheet having a wearer-facing side, a liquid impermeable backsheet having a garment-facing side, an absorbent structure disposed between the topsheet and the backsheet, and the nonwoven according to claim 1.

16. An absorbent article comprising a liquid permeable topsheet having a wearer-facing side, a liquid impermeable backsheet having a garment-facing side, an absorbent structure disposed between the topsheet and the backsheet, wherein the topsheet comprises the nonwoven according to claim 1 such that the first nonwoven layer of the nonwoven forms at least part of the wearer-facing side.

17. An absorbent article comprising a liquid permeable topsheet having a wearer-facing side, a liquid impermeable backsheet having a garment-facing side, an absorbent structure disposed between the topsheet and the backsheet, wherein the backsheet comprises the nonwoven according to claim 1 such that the first nonwoven layer of the nonwoven forms at least part of the garment-facing side.

18. A nonwoven comprising:
a first nonwoven layer comprising cellulose-based fibers, wherein the first nonwoven layer comprises a plurality of apertures, the plurality of apertures formed by mechanically aperturing at least one moisturized area having a water content of at least about 20% by weight of the nonwoven in the moisturized area, prior to aperturing, and a plurality of apertures, wherein the plurality apertures have a minimum aperture distance between two adjacent apertures which has a relative standard deviation no greater than about 40%, wherein the apertures have an aperture size no greater than about 2.2 mm$^2$, and wherein the apertures have an aspect ratio no greater than about 2.5, wherein a mean of shortest distances, the shortest distance being between an aperture's centroid and the centroid of its nearest neighboring aperture and above 1 mm, is calculated as the minimum aperture distance and the standard deviation of the shortest distances divided by the mean and multiplied by 100 is the relative standard deviation; wherein a mean of aperture areas is calculated as aperture size and the standard deviation of the aperture areas divided by the mean and multiplied by 100 is the relative standard deviation; and wherein a mean of aperture aspect ratios is calculated as aspect ratio, provided that apertures with sizes below 0.10 mm$^2$ and incomplete openings are excluded.

19. A nonwoven comprising:
a first nonwoven layer comprising cellulose-based fibers, wherein the first nonwoven layer comprises a plurality of apertures, the plurality of apertures formed by pin-hole aperturing at least one moisturizing area having a water content of at least about 20% by weight of the nonwoven in the moisturized area, prior to aperturing, and a plurality of apertures, wherein the apertures have an aperture size no greater than about 2.2 mm$^2$, wherein the plurality of apertures have a minimum aperture distance between two adjacent apertures which has a relative standard deviation no greater than about 40%, wherein a mean of shortest distances, the shortest distance being between an aperture's centroid and the centroid of its nearest neighboring aperture and above 1 mm, is calculated as the minimum aperture distance and the standard deviation of the shortest distances divided by the mean and multiplied by 100 is the relative standard deviation, wherein a mean of aperture areas is calculated as the aperture size, provided that apertures with sizes below 0.10 mm$^2$ and incomplete openings are excluded.

* * * * *

UNITED STATES PATENT AND TRADEMARK OFFICE
CERTIFICATE OF CORRECTION

| | |
|---|---|
| PATENT NO. | : 11,850,820 B2 |
| APPLICATION NO. | : 17/231132 |
| DATED | : December 26, 2023 |
| INVENTOR(S) | : Xiaoxin Liu et al. |

It is certified that error appears in the above-identified patent and that said Letters Patent is hereby corrected as shown below:

On the Title Page

Before Item (51) Int. Cl., please insert the following:
-- (30) Foreign Application Priority Data
April 16, 2020 (CN) PCT/CN2020/085097 --

Signed and Sealed this
Twelfth Day of November, 2024

Katherine Kelly Vidal
*Director of the United States Patent and Trademark Office*